United States Patent
Ngoi et al.

(10) Patent No.: US 6,525,331 B1
(45) Date of Patent: Feb. 25, 2003

(54) BALL GRID ARRAY (BGA) PACKAGE ON-LINE NON-CONTACT INSPECTION METHOD AND SYSTEM

(75) Inventors: Bryan Kok Ann Ngoi, Singapore (SG); Fan Hua, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 09/452,160

(22) Filed: Dec. 1, 1999

(51) Int. Cl.$^7$ .............................................. G01N 21/86
(52) U.S. Cl. ............................ 250/559.34; 250/237 G; 250/559.46; 356/237.5; 382/149
(58) Field of Search ........................ 250/559.34, 237 G, 250/559.45, 559.46; 356/237.4, 237.2, 237.5, 605, 618, 616; 382/145, 147, 148, 149, 150

(56) References Cited

U.S. PATENT DOCUMENTS

| | | | |
|---|---|---|---|
| 5,003,600 A | * 3/1991 | Deason et al. ................. 380/54 |
| 5,343,294 A | * 8/1994 | Kuchel et al. ............... 356/376 |
| 5,465,152 A | 11/1995 | Bilodeau et al. ............. 356/371 |
| 5,574,668 A | 11/1996 | Beaty .......................... 364/558 |
| 5,636,025 A | * 6/1997 | Bieman et al. .............. 356/374 |
| 5,652,658 A | 7/1997 | Jackson et al. ............. 356/398 |
| 5,815,275 A | 9/1998 | Svetkoff et al. ............ 356/376 |
| 5,835,223 A | * 11/1998 | Zwemer et al. ............. 356/371 |
| 5,898,486 A | * 4/1999 | Chesko, Sr. et al. ....... 356/35.5 |
| 5,969,819 A | * 10/1999 | Wang .......................... 356/371 |
| 6,084,712 A | * 7/2000 | Harding ...................... 359/618 |
| 6,268,923 B1 | * 7/2001 | Michniewicz et al. ...... 356/512 |

FOREIGN PATENT DOCUMENTS

EP           0638801 A1    8/1993        G01N/21/88

* cited by examiner

Primary Examiner—Stephone B. Allen
Assistant Examiner—Eric Spears
(74) Attorney, Agent, or Firm—Burns, Doane, Swecker & Mathis, LLP

(57) ABSTRACT

A method and apparatus is disclosed for non-contact, on-line inspection of objects including a ball grid array package by means of a shadow moiré technique combined with a novel flash phase-shifting method. The grid pitch size, ball height, ball diameter, missing ball, coplananity can be determined or measured within several seconds. The apparatus includes a camera for viewing the object, a plurality of light sources arranged in a line for illuminating the object to be inspected, a frame grabber for capturing images of the object, an I/O adapter card for controlling the light sources and a personal computer for data processing. The individual components are integrated into system which provides a three dimensional map which is obtained quantitatively using a novel algorithm. The system can provide coplananity data, as well as data relating to grid pitch, ball height, ball diameter, and missing ball information.

14 Claims, 5 Drawing Sheets

○ ball
● no ball

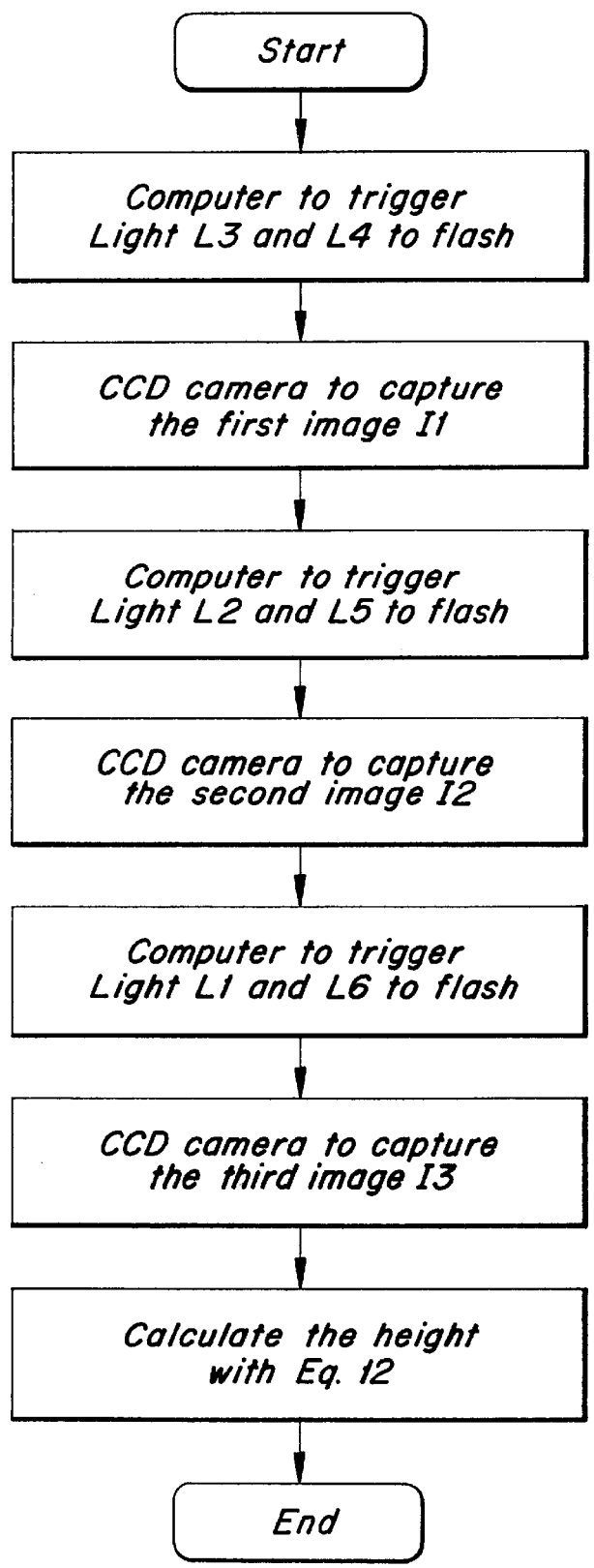

BALL GRID ARRAY (BGA) PACKAGE ON-LINE NON-CONTACT INSPECTION METHOD AND SYSTEM

FIELD OF THE INVENTION

The present invention relates to a non-contact on-line inspection method and apparatus for the grid pitch size, solder ball height, diameter, missing ball and coplanarity of a ball grid array (BGA) package, which are being widely employed in the microelectronics industry. The fast flash phase shifting method and the novel structural design of the present invention provide for the fast calculation of various parameters at a very fast speed and with high precision and accuracy.

BACKGROUND OF THE INVENTION

In the microelectronics industry, chip makers improve chip performance by using ever smaller line widths to pack millions of transistors on a chip. Today more than three million transistors are packed in a chip, and the number is expected to increase to one hundred million in the near future. In turn, the packaging technology must provide more input/output connections with a finer pitch to accommodate the new chips. Conventional packaging techniques cannot meet this requirement. New advanced packaging techniques are being proposed and studied. The ball grid array (BGA) is one of the latest packaging techniques, and it has been studied widely in recent years. A ball grid array (BGA) is an array of solderable balls placed on a chip carrier. The balls contact a printed circuit board in an array configuration where, after reheat, they connect the chip to the printed circuit board. BGA's are typically used in 40, 50, and 60 mil spacings with regular and staggered array patterns. So far, this kind of package has been utilized by industry, and it has been established as part of an industrial standard, which also includes such things as ball count, ball dimension and height, coplanarity, lead pitch, body size, etc. These specifications are very important in product quality control. They greatly effect reliability. For example, defective balls adversely affect the overall reliability of the bonds created by the soldered ball process. If a ball has an insufficient height, then no electrical connection is made between the ball and the corresponding pad of the circuit board. On the other hand, if a ball has excessive height an undesired connection may occur.

The separation between the ball tips and the flat surface are referred to as coplanarity. Generally, if a chip is placed on a flat surface, such as a printed circuit board, only three balls will make contact with the board (three points defined a plane). Other balls may contact or nearly contact the PCB surface depending on chip tolerances, on the size of the balls, on the flatness of the chip, etc. The closer to the surface all the balls are the more reliable will be the interconnection of all the leads once the solder has been reflowed. The magnitude of the coplanarity parameter is a predictor of how well chip leads can be accurately and reliably soldered to their corresponding pads on a printed circuit board and as a diagnostic measure for determining when the elements of the package fabrication process are going out of control. All these issues present important problems for non-contact on-line inspection.

The ball position, ball diameter and package dimension can be obtained by means of an image processing technique. The most difficult task is to measure the ball height. Some prior art methods of non-contact and contact measurement have been developed, but there are some shortcomings in these prior art techniques. Therefore, it is an objective of the present invention to provide a sufficiently high, rapid and accurate method and apparatus for measuring BGA characteristics.

U.S. Pat. No. 5,652,658 describes an optical, non-contact system for measuring the height of a BGA solders ball. The system uses a three dimensional scanner, which works on a triangulation principle, to gather data which is analysed to determine height. The grid array to be scanned is placed upon a fixture above a motion control table. The motion control system is controlled by a personal computer, and it has a high resolution. An automatic pick and place device is used to load the grid array packages on the fixture. The fixture consists of a plate with a cavity having the size of the grid array package being inspected. In addition to the height and position measurement, the measurements of grid pitch, ball diameter, ball position, and coplanarity can be performed. The problems with this arrangement include low efficiency due to the adoption of a point scanning method, and a high cost due to the requirement for a high resolution moving stage and a high-speed data acquisition system.

U.S. Pat. No. 5,815,275 describes a method and system, which utilizes a triangulation based laser line scanning principle for BGA measurement. A scanning beam is incident at a normal angle to the X, Y inspection plane with a scan line oriented at a 45 degree angle. The motion of the imaging head along the axis is used to acquire line scan images. The problem with this technique is a low efficiency due to the requirement for a high resolution moving stage.

U.S. Pat. No. 5,574,688 describes a contact method for measuring ball grid arrays. In this method, an array of touch sensors is brought in contact with a ball grid array. A linear actuator moves the array of touch sensors. The position of the linear actuator is known very precisely. As the touch sensors encounter the ball grid array, they provide a signal to a computer system indicating that an element on the ball grid array has been encountered. The computer notes the position of the linear actuator and the particular sensor in the touch sensor array that is providing the signal. The problem with this arrangement is a low efficiency due to the requirement for a mechanical movement structure, and a high cost due to the requirement for a high resolution moving stage. In addition, the rigid structure of sensor array cannot accommodate the different kinds of BGA patterns.

The field of three-dimensional methods includes useful techniques for on-line inspection such as projected grating and the use of a shadow moiré. The shadow moiré techniques are simple and cost effective, but apart from this, the measurement is performed very close to the actual location of co-planarity. Classical shadow moiré, therefore, cannot be applied directly due to its low accuracy.

SUMMARY OF THE INVENTION

In the present invention, a novel flash phase shifting method combined with a computer aided shadow moiré technique is used to obtain quantitative height data for a BGA. The novel phase shifting technique and algorithm enable the present invention to do on-line inspection of a BGA and overcome the above-described problems of the prior art.

More specifically, in the present invention, a plurality of light sources with the same specifications is employed. Preferably, there are six light sources arranged in a line. The illumination from the light sources is incident on the surface of an integrated circuit or chip at known angles. A test chip is placed on the surface of a uniformly space grating. A recording camera is preferably positioned on the other side of the grating to view the chip through the grating. The light sources are positioned so that the line between them and the center of the test object surface and the optic axis of the camera form a plane. The lines of the grating are normal to this plane. The method and apparatus of the present invention relies on the shadow of the grating lines to interfere with the grating lines themselves to produce fringes known as the moiré effect. The light sources flash and an imaging device captures an image of the illuminated object. The image data is processed according to a novel algorithm. A relatively fast and highly accuracy on-line inspection of a BGA can be achieved. This invention is not only suitable for BGA inspection but, it is also applicable to fast non-contact three-dimensional profilometry as well as flatness measurement.

BRIEF DESCRIPTION OF DRAWINGS

FIG. 8 is a flow diagram of the method of the present invention.

DETAILED DESCRIPTION OF THE PREFERRED EMBODIMENTS

Figure 1:
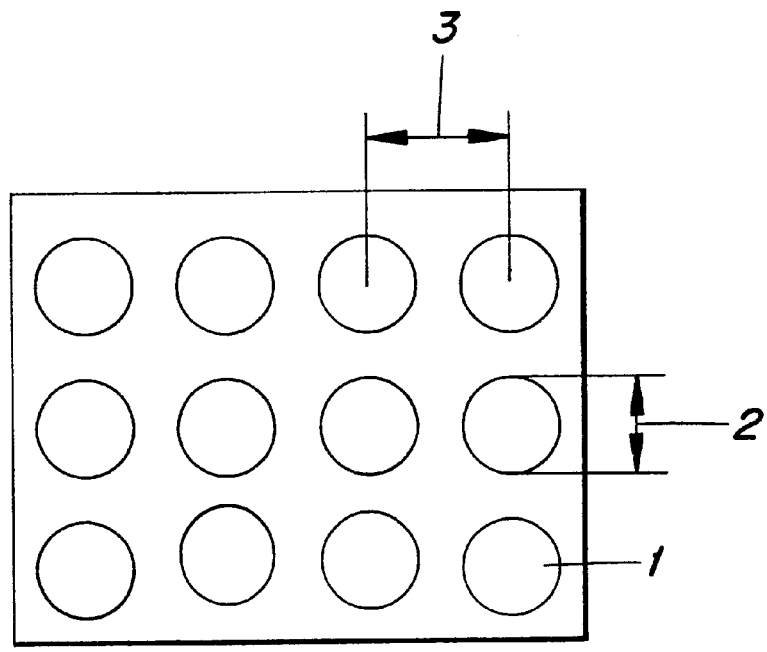
FIG. 1 is a schematic plan view of a three by four ball grid array.

FIG. 1 is a schematic plan view of a three by four ball grid array or BGA which includes twelve balls 1. In the ball grid array, the distances between the center of the balls or pitch 3 are preferably equal, and the diameters 2 of the balls 1 are also preferably equal. In actual practice this is often not the case.

Figure 2:
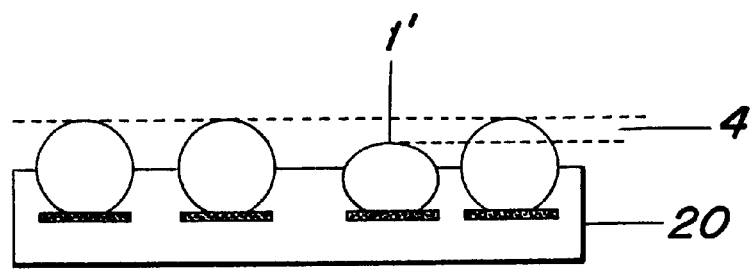
FIG. 2 is a schematic diagram of a front view of the ball grid array in FIG. 1.
Figure 3:
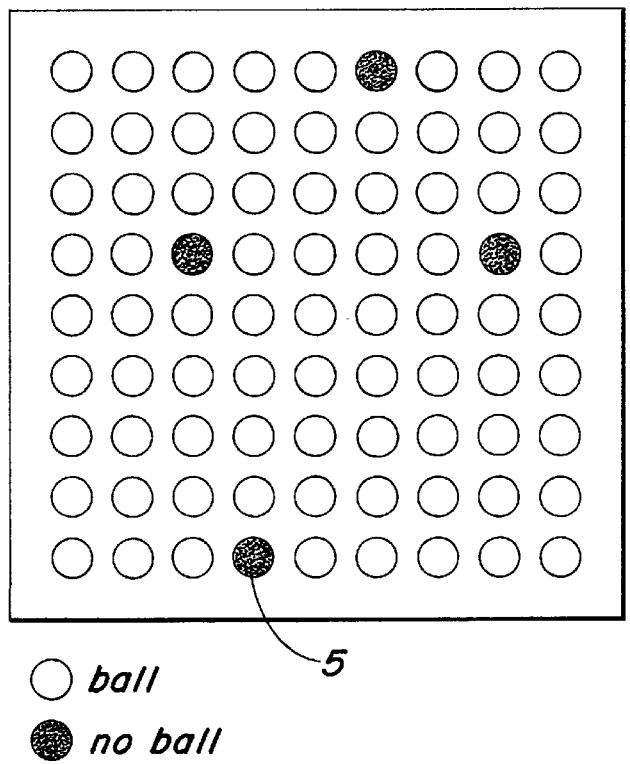
FIG. 3 is a schematic plan view of a BGA with index pads selected from the totality of signal pads.

FIG. 2 is a schematic diagram of a front view of the ball grid array in FIG. 1, which illustrates the height of the balls 1. It can be readily appreciated that the height 4 of ball 1' disposed on the chip carrier 20 is different from the height of the other balls 1 which is often the case.

The apparatus and method of inspection according to the present invention enables the array of balls 1 to be inspected with high speed and high accuracy. Such a method is carried out by means of an inspection machine illustrated in FIG. 5. An IC chip of BGA package 10 is placed on a grating 11, which lies on a layer of flat optical glass substrate. A camera 13 is positioned on the bottom of a box to view the IC chip 10 through the grating 11. An illumination device 12 includes six light sources L1, L2, L3, L4, L5, L6 which are preferably positioned on both sides of the camera 13 in accordance with the novel phase shift algorithm to illuminate the IC package 10. A video frame is produced from the camera 13, and a frame grabber 9 digitizes the video frame. A computer 7 according to the algorithm of the present invention then processes the digitized frame. An entire map of all the ball heights 4, the diameter 2 and the pitch 3 can be obtained automatically. The inspection process only requires that the IC package 10 be placed on the surface of grating 11. The inspection process has no physical effect on the IC package 10.

The first objective of the inspection method is to obtain the heights 4 of the balls 1. A shadow moiré is used to measure the heights 4 of balls 1. An optical analysis of the shadow moiré will now be described. In this optical analysis, the abbreviations tan and tg will be used. The abbreviation tg is commonly used outside the United States as the abbreviation for tangent, instead of tan. Accordingly, in the present application the abbreviations tg and tan are interchangeably used, and they both mean tangent.

Figure 4:
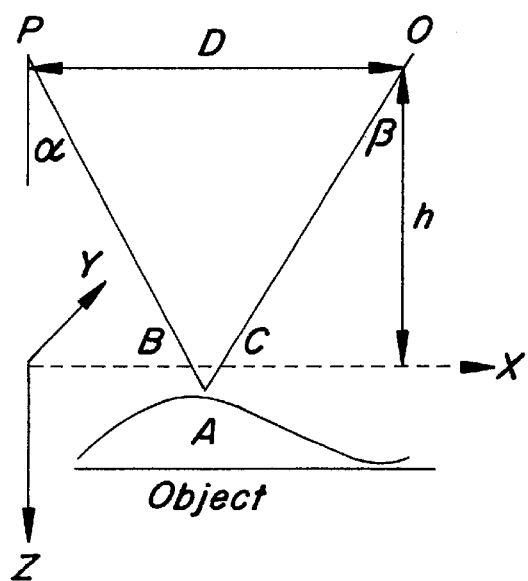
FIG. 4 is a schematic diagram of an object and a grating for producing a basic shadow moiré.

FIG. 4 shows a schematic diagram of the optical configuration of the classical shadow moiré measuring technique. Typically, a uniformly spaced grating is mounted as close as possible to the front surface of the test object. A recording camera is set up point O to view the test object through the grating which is located in a plane defined by the x and y axes. A light source is located at point P. This method relies on the shadow of the grating lines interfering with the grating lines themselves to produce fringes known as the moiré effect. The advantage of this method is that a hypothetical observer standing in the vicinity of the recording camera would see the displacement fringes in real time. Since the sinusoidal grating with a pitch p is employed, its transparent ratio function can be expressed as:

$$T(x) = \frac{1}{2}\left(1 + \cos\frac{2\pi x}{p}\right) \quad (1)$$

In order to simplify the equation, the light source and the observation point are positioned at the same height from the reference plane (the grating plane). The light from light source at point $P(x_p, y_p, z_p)$ passes through the grating from point $B(x_B, y_B, 0)$ to reach the surface of the object at point $A(x, y, z)$. The scattered light passes again through the grating at the point $C(x_c, y_c, 0)$ and goes to observation point $O(x_o, y_o, z_o)$. The intensity observed at the observation point O is given by:

$$I_o(x_o, y_o, z_o) = K\left(1 + \sin\frac{2\pi x_B}{p}\right)\left(1 + \sin\frac{2\pi x_C}{p}\right) \quad (2)$$

$$= K\left(1 + \sin\frac{2\pi}{p}\frac{xh}{h+z}\right)\left(1 + \sin\frac{2\pi}{p}\frac{Dz + xh}{h+z}\right)$$

where K is a factor which depends on the surface quality around point A as well as its position and the intensity of the light source. After a filtering operation, the term corresponding to the moiré pattern from Equation (2), is given by:

$$I(x, y, z) = a(x, y) + b(x, y)\cos\left[\frac{2\pi}{p}\left(\frac{Dz}{h+z}\right)\right] \quad (3)$$

$$= a(x, y) + b(x, y)\cos\varphi$$

when $$\varphi = 2n\pi \quad n = 0, \pm 1, \pm 2, \ldots \quad (4)$$

Corresponding height z can be given as:

$$z = \frac{nph}{D - pn} \quad (5)$$

where D is the distance between the light source at point P and the observer located at point O, p is the pitch of the grating, h is the height from the observer to the grating plane, n is the fringe order.

From Equation (5), one can see that the classical shadow moiré method has the disadvantage of low resolution and uncertainty in determining whether the test object is convex or concave. From Equation (3), one can see that the shadow moiré fringes have sinusoidal intensity distribution. This problem, therefore, can be solved by means of the phase shifting technique of the present invention. The conventional method is to calculate the phase through several images with different phase values, which will improve the accuracy greatly and allow the quantitative data to be obtained automatically. One common phase shifting algorithm requires three images to be recorded; between each recording the phase is shifted respectively by 0, 2π/3, 4π/3 rad. The wrapped phase can be obtained by:

$$\varphi(x, y, z) = \tan^{-1} \frac{\sqrt{3}(I_3 - I_2)}{2I_1 - I_2 - I_3} \quad (6)$$

where $I_1$, $I_2$ and $I_3$ express the light intensity corresponding to phase 0, 2π/3, 4π/3 respectively.

The real phase, which represents the real height of the test object, can be obtained through an unwrapping procedure. Phase unwrapping methods have been extensively researched. The algorithm employed by most researchers consists of a row and a column search of the distribution first by resolution of the vertical discontinuities and then by that of the horizontal discontinuities. The method of the present invention, however, is entirely different from classical phase shift just described.

In the classical shadow moiré patterns, the fringe represents the points with equal height. Equation (5) expresses the height of each fringe order. The point between the two fringes cannot be certain. This causes low measurement accuracy. In order to promote the accuracy and obtain the quantitative data automatically, a phase-shifting technique is employed. The real problem in shadow moiré is how to introduce a phase shift δϕ. The solution is not evident. From Equation (3) one can see there are four parameters that affect the phase ϕ. So there are four different ways to change the phase ϕ into ϕ+δϕ. They are: (1) changing D into D+δD; (2) h into h+δh; (3) p into p+δp; (4) z into z+δz. One way is to change z to introduce different phase values. The shortcoming of this method is that it is slow because of the need for mechanical movement between the test object and the grating. It also cannot meet the industry's on-line inspection requirement.

The inventors, however, have discovered a novel phase-shifting method, which utilizes flash phase shifting. This flash phase shifting technique is implemented using the system depicted in FIG. 5. Referring again to FIG. 5, the plurality of light sources L1, L2, L3, L4, L5, L6 with the same specifications are symmetrically placed on both sides of the viewing point or CCD camera 13 with different illuminating angles to the test object. The illuminating angles are $\theta_1$, $\theta_2$ and $\theta_3$, respectively. Each pair of light source L1-L6, L2-L5, L3-L4 flashes in turn to illuminate the object or BGA or chip 10, and correspondingly the camera 13 captures the images. The image acquisition and processing system preferably includes the CCD camera 13, a frame grabber a and a personal computer. The image processing system is utilized to capture image and process data. The entire period of grabbing all the images take about 120 milliseconds. Subsequent processing of the images according to the algorithm yields the height map of the object 10. The data processing time depends on the processor speed. Commonly, it is within several seconds. This method is, therefore, suitable for on-line inspection.

The implementation of the algorithm will now be described. In a practical situation h>>z, and Equation (3) can be simplified:

$$I(x, y, z) = a(x, y, z) + b(x, y, z)\cos\left(\frac{2\pi}{p}\frac{D}{h}z\right) \quad (7)$$

$$= a(x, y, z) + b(x, y, z)\cos(\phi tg\theta)$$

where:

$$\phi = \frac{2\pi}{p}z$$

From Equation (7) there are three unknown components so three intensity measurements are required to obtain the phase ϕ. Changing the illuminating angle θ to $\theta_1$, $\theta_2$ and $\theta_3$, respectively. The corresponding images are expressed as $I_1$, $I_2$ and $I_3$, respectively.

$$\begin{cases} I_1(x, y) = a(x, y) + b(x, y)\cos(\phi tg\theta_1) \\ I_2(x, y) = a(x, y) + b(x, y)\cos(\phi tg\theta_2) \\ I_3(x, y) = a(x, y) + b(x, y)\cos(\phi tg\theta_3) \end{cases} \quad (8)$$

Assuming, $$tg\ \theta_1 = m_1,\ tg\ \theta_2 = m_2,\ tg\ \theta_3 = m_3 \quad (9)$$

And setting $m_2 = 3m_1$, $m_3 = 5m_1$ $$\frac{I_3 - I_2}{I_2 - I_1} = 2\cos 2m_1\phi \quad (10)$$

$$\phi = \frac{1}{2m_1}\arccos\frac{I_3 - I_2}{2(I_2 - I_1)} \quad (11)$$

$$z(x, y) = \frac{p}{4\pi tg\theta_1}\arccos\frac{I_3 - I_2}{2(I_2 - I_1)} \quad (12)$$

Thus, the heights of all points referenced to the grating plane can be obtained.

After the heights of all the points are obtained the coplanarity can be calculated. Grid pitch size, ball diameter, missing ball can be obtained by means of digital image processing technique. For example, an edge detected algorithm can be used to determine the ball edges; the centers can be obtained through a centroid algorithm; and grid pitch size and ball diameter can be obtained after the ball edges and the ball centers have been determined.

Figure 5:
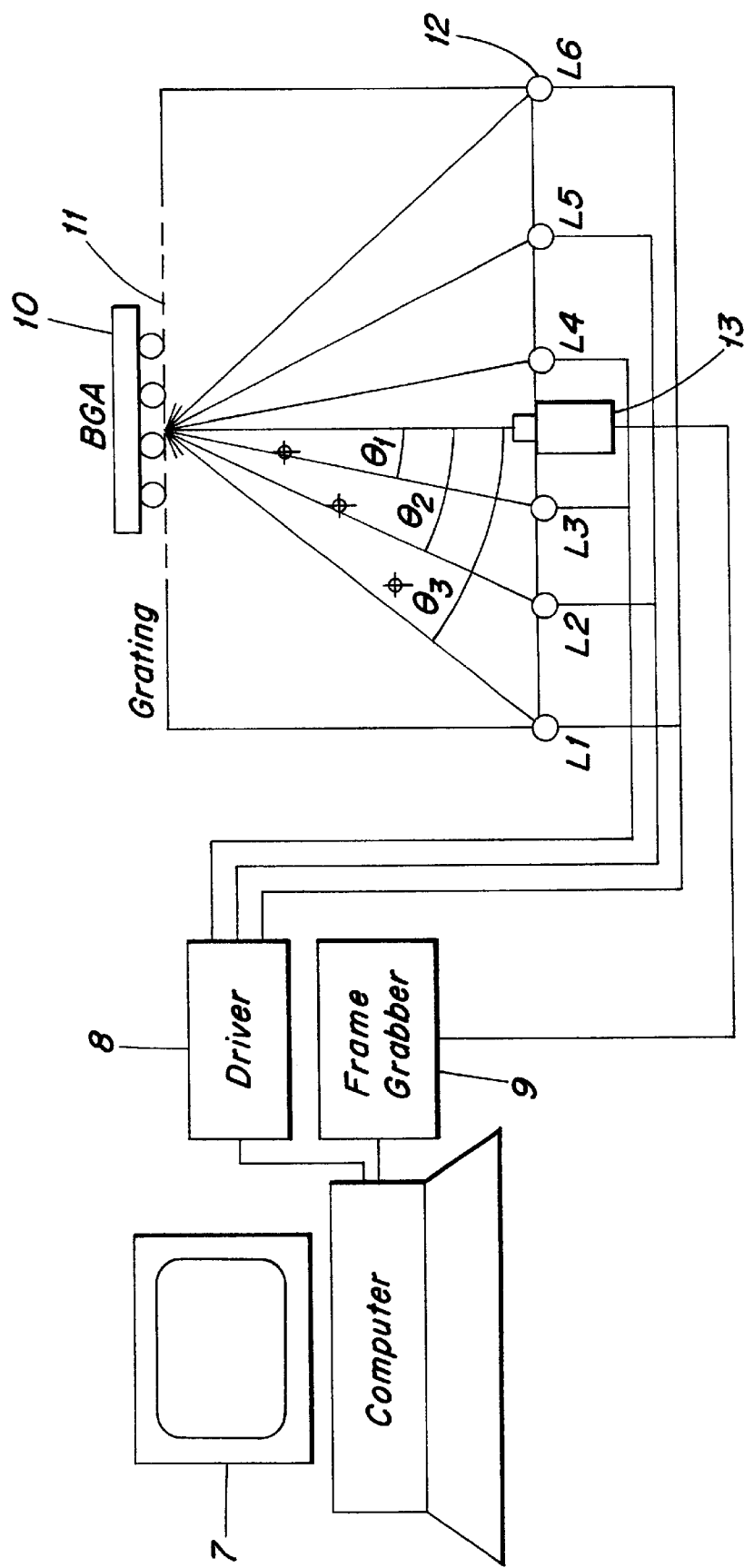
FIG. 5 is a schematic diagram of the flash phase shifting shadow moiré set up of the present invention.

In FIG. 5, the grating 11 is preferably a sinusoidal distribution transmitted type with an optical glass substrate. The light sources L1, L2, L3, L4, L5 and L6 have either a spot or linear configuration and are of an intensity adequate to the sensitivity of the camera. In the preferred embodiment, a wavelength of 680 nm red light is utilized. An increase in the light intensity results in better performance.

Figure 6:
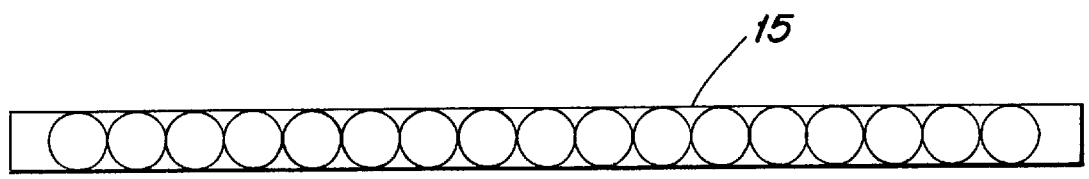
FIG. 6 depicts the structure of a linear light source constructed from an LED array.
Figure 7:
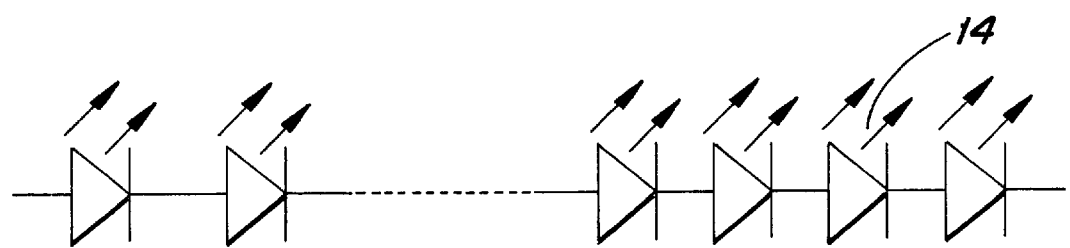
FIG. 7 depicts the electronic connections of LED's.

In order to enhance the light intensity, a plurality of ultra-bright light emitting diodes (LED) may be arranged in a line to act as a line light source 15 as depicted in FIG. 6 which shows such linear light source. FIG. 7 shows the electronic connection between the LED's.

In the present invention, the six light sources are assembled in accordance with the relationship of tg $\theta_2$=3 tg $\theta_1$, tg $\theta_3$=5tg $\theta_1$. In the preferred embodiment, the angles are 11 degrees, 29 degrees and 45 degrees, respectively. The camera 13 is a standard CCD camera with a lens having a 16 mm focal length. An extension may be installed between the camera 13 and the lens to make the full use of the camera's resolution. The system also preferably includes a constant current driver 8 which is designed for constant light intensity. The light sources are controlled by the computer 7 through an I/O adapter card. The software is preferably designed as Windows application, which works on the Windows NT/95 platform, and the inspection procedure is carried out automatically under control of the software.

What is claimed is:

1. A system for the on-line inspection of the surface of objects including ball grid arrays, comprising:

a grating, disposed near the object, for forming a shadow moiré fringe pattern;

means for imaging the object;

means for generating light from at least three light sources disposed along a line at predetermined angles $\theta_1$, $\theta_2$, $\theta_3$, which are defined by the locations of each of the light sources, the object and the means for imaging the object, wherein the illumination from the light sources is caused to individually flash in turn and is directed through the grating and onto the surface of the object; and means for processing the images of the object to determine a measurement related to the surface of the object.

2. The apparatus according to claim 1, wherein the light sources of said means for generating light include a plurality of light emitting diodes.

3. The apparatus according to claim 1 wherein the angles $\theta_1,\theta_2,\theta_3$ equal 11 degrees, 29 degrees and 45 degrees, respectively.

4. The apparatus according to claim 1, wherein said means for imaging includes a frame grabber to sequentially capture images and carry on high speed non-contact inspection.

5. The apparatus according to claim 1, wherein said grating includes a transmission grating made from an optical glass.

6. The apparatus according to claim 1, wherein said means for generating light includes a constant current light source driver.

7. The apparatus according to claim 1, wherein said means for imaging includes a CCD camera.

8. A method for the on-line inspection of the surface of objects including ball grid arrays, comprising the steps of:

generating light from at least three light sources disposed along a line at predetermined angles $\theta_1$, $\theta_2$, $\theta_3$, which are defined by the locations of each of the light sources, the object and means for imaging the object, wherein the illumination from the light sources is caused to individually flash in turn and is directed onto the surface of the object;

forming a fringe pattern;

imaging the fringe pattern when the object is illuminated by the light sources; and processing the images to determine a measurement related to the surface of the object.

9. The method according to claim 8, wherein the light is generated from a plurality of light emitting diodes.

10. The method according to claim 8 wherein the angles $\theta_1,\theta_2,\theta_3$ equal 11 degrees, 29 degrees and 45 degrees, respectively.

11. The method according to claim 8, wherein said imaging includes using a frame grabber to sequentially capture images and carry on high speed non-contact inspection.

12. The method according to claim 8, which includes a transmission grating made from an optical glass.

13. The method according to claim 8, wherein generating light includes using a constant current light source driver.

14. The method according to claim 8, wherein said imaging includes using a CCD camera.

* * * * *